(12) United States Patent
Lyslo et al.

(10) Patent No.: US 12,318,497 B2
(45) Date of Patent: Jun. 3, 2025

(54) HARD-SURFACE DISINFECTION SYSTEM

(71) Applicant: Surfacide, LLC, Waukesha, WI (US)

(72) Inventors: Waldemar John Lyslo, Naperville, IL (US); Mark Howard Schwartz, Rochester, NY (US); Stephen Boyd Pettis, Rochester, NY (US)

(*) Notice: Subject to any disclaimer, the term of this patent is extended or adjusted under 35 U.S.C. 154(b) by 0 days.

(21) Appl. No.: 18/345,929

(22) Filed: Jun. 30, 2023

(65) Prior Publication Data

US 2023/0338595 A1 Oct. 26, 2023

Related U.S. Application Data

(63) Continuation of application No. 17/165,751, filed on Feb. 2, 2021, now abandoned, which is a continuation
(Continued)

(51) Int. Cl.
*A61L 2/10* (2006.01)
*A61L 2/24* (2006.01)
(Continued)

(52) U.S. Cl.
CPC ........ *A61L 2/10* (2013.01); *A61L 2/24* (2013.01); *A61L 9/20* (2013.01); *H05B 45/10* (2020.01); *H05B 45/14* (2020.01); *H05B 47/19* (2020.01); *A61L 2202/14* (2013.01); *A61L 2202/16* (2013.01); *A61L 2202/25* (2013.01); *A61L 2209/111* (2013.01)

(58) Field of Classification Search
CPC ..... A61L 2/10; A61L 2/24; A61L 9/20; A61L 2202/14; A61L 2202/16; A61L 2202/25; A61L 2209/111; H05B 45/10; H05B 45/14; H05B 47/19
See application file for complete search history.

(56) References Cited

U.S. PATENT DOCUMENTS 4,115,280 A 9/1978 Pratt, Jr.
4,181,929 A 1/1980 Barber et al.
(Continued)

FOREIGN PATENT DOCUMENTS

DE 7223023 U 12/1972

OTHER PUBLICATIONS

Deal, J.L., M.D. et al., "Alterations of Bacteria Colony Counts in the Inanimate Environment of an Intensive Care Unit By Use of the Tru-D Device," UV Solutions NW, Bellevue, Washington, link labeled "Tm-D Bacteria Trial (203KB PDF)" from http://www.uvsolutionsnw.com/ultraviolet-effectivenessresearch.html, Apr. 15, 2002 to Aug. 1, 2002, 8 pages.

*Primary Examiner* — David A Vanore
(74) *Attorney, Agent, or Firm* — McKinley IP LLC

(57) ABSTRACT

UV hard-surface disinfection system that is able to disinfect the hard surfaces in a room, while minimizing missed areas due to shadows by providing multiple UV light towers that can be placed in several areas of a room such that shadowed areas are eliminated and that can be transported by a cart that is low to the ground such that the towers may be loaded and unloaded easily by a single operator. The system is able to be controlled remotely, such that during activation of the system, no operator is present, and to automatically cut power to all towers in the event that a person enters the room.

10 Claims, 10 Drawing Sheets

Related U.S. Application Data of application No. 16/911,123, filed on Jun. 24, 2020, now Pat. No. 10,933,149, which is a continuation of application No. 16/779,351, filed on Jan. 31, 2020, now Pat. No. 10,729,797, which is a continuation of application No. 16/125,642, filed on Sep. 7, 2018, now Pat. No. 10,568,981, which is a continuation of application No. 15/699,219, filed on Sep. 8, 2017, now Pat. No. 10,092,665, which is a continuation of application No. 15/425,585, filed on Feb. 6, 2017, now Pat. No. 9,782,505, which is a continuation of application No. 15/018,440, filed on Feb. 8, 2016, now Pat. No. 9,592,312, which is a continuation of application No. 14/540,869, filed on Nov. 13, 2014, now Pat. No. 9,272,059, which is a continuation of application No. 14/043,465, filed on Oct. 1, 2013, now Pat. No. 8,895,939, which is a continuation of application No. 12/963,590, filed on Dec. 8, 2010, now Pat. No. 8,575,567.

(60) Provisional application No. 61/324,257, filed on Apr. 14, 2010, provisional application No. 61/267,805, filed on Dec. 8, 2009.

(51) Int. Cl.
*A61L 9/20* (2006.01)
*H05B 45/10* (2020.01)
*H05B 45/14* (2020.01)
*H05B 47/19* (2020.01)

(56) References Cited

U.S. PATENT DOCUMENTS

| | | | |
|---|---|---|---|
| 4,220,981 A | 9/1980 | Koether | |
| 4,234,820 A | 11/1980 | Widmayer | |
| 4,829,608 A | 5/1989 | Stevens et al. | |
| 5,238,239 A | 8/1993 | LaChapelle | |
| 5,239,239 A | 8/1993 | Biegel et al. | |
| 5,345,150 A | 9/1994 | Biegel | |
| 5,404,080 A | 4/1995 | Quazi | |
| 5,517,388 A | 5/1996 | Hutchisson | |
| 5,806,963 A | 9/1998 | Miller et al. | |
| 5,957,959 A | 9/1999 | Rissmaney et al. | |
| 6,132,784 A | 10/2000 | Brandt et al. | |
| 6,524,529 B1 | 2/2003 | Horton, III | |
| 6,656,424 B1 | 12/2003 | Deal | |
| 6,911,177 B2 | 6/2005 | Deal | |
| 7,612,492 B2 | 11/2009 | Lestician | |
| 7,783,383 B2 | 8/2010 | Eliuk et al. | |
| 7,923,707 B2 | 4/2011 | Garcia et al. | |
| 8,029,739 B2 | 10/2011 | Field et al. | |
| 8,110,819 B2 | 2/2012 | Bovarski et al. | |
| 8,446,341 B2 | 5/2013 | Amirparviz et al. | |
| 8,575,567 B2 * | 11/2013 | Lyslo | H05B 45/14 250/455.11 |
| 8,895,939 B2 * | 11/2014 | Lyslo | H05B 45/14 422/23 |
| 9,023,274 B2 | 5/2015 | Garner et al. | |
| 9,043,217 B2 | 5/2015 | Cashman et al. | |
| 9,272,059 B2 * | 3/2016 | Lyslo | H05B 47/19 |
| 9,592,312 B2 * | 3/2017 | Lyslo | A61L 2/24 |
| 9,782,505 B2 * | 10/2017 | Lyslo | A61L 9/20 |
| 10,092,665 B2 * | 10/2018 | Lyslo | A61L 2/10 |
| 10,568,981 B2 * | 2/2020 | Lyslo | A61L 2/24 |
| 10,729,797 B2 * | 8/2020 | Lyslo | H05B 45/10 |
| 10,933,149 B2 * | 3/2021 | Lyslo | H05B 45/10 |
| 2002/0085947 A1 | 7/2002 | Deal | |
| 2002/0100878 A1 | 8/2002 | Summers et al. | |
| 2003/0030011 A1 | 2/2003 | Brown et al. | |
| 2003/0146082 A1 | 8/2003 | Gibson et al. | |
| 2003/0170151 A1 | 9/2003 | Hunter et al. | |
| 2005/0022330 A1 | 2/2005 | Park et al. | |
| 2006/0154642 A1 | 7/2006 | Scannell, Jr. | |
| 2006/0216193 A1 | 9/2006 | Johnson et al. | |
| 2006/0284109 A1 | 12/2006 | Scheir et al. | |
| 2007/0053188 A1 | 3/2007 | New et al. | |
| 2007/0231192 A1 | 10/2007 | Jung et al. | |
| 2009/0143842 A1 | 6/2009 | Cumbie et al. | |
| 2009/0184268 A1 | 7/2009 | Garcia et al. | |
| 2009/0191100 A1 | 7/2009 | Deal | |
| 2010/0082193 A1 | 4/2010 | Chiappetta | |
| 2010/0104471 A1 | 4/2010 | Harmon et al. | |
| 2011/0168898 A1 | 7/2011 | Statham et al. | |
| 2011/0215261 A1 * | 9/2011 | Lyslo | A61L 2/10 250/492.1 |
| 2014/0034849 A1 * | 2/2014 | Lyslo | A61L 2/24 250/492.1 |
| 2015/0069269 A1 * | 3/2015 | Lyslo | H05B 45/10 250/492.1 |
| 2016/0151524 A1 * | 6/2016 | Lyslo | A61L 9/20 250/492.1 |
| 2017/0143859 A1 * | 5/2017 | Lyslo | A61L 2/24 |
| 2018/0008736 A1 * | 1/2018 | Lyslo | H05B 47/19 |
| 2019/0001007 A1 * | 1/2019 | Lyslo | H05B 47/19 |
| 2020/0171185 A1 * | 6/2020 | Lyslo | A61L 2/10 |
| 2020/0330630 A1 * | 10/2020 | Lyslo | A61L 2/24 |
| 2021/0178000 A1 * | 6/2021 | Lyslo | H05B 45/10 |
| 2023/0338595 A1 * | 10/2023 | Lyslo | A61L 2/10 |

* cited by examiner

HARD-SURFACE DISINFECTION SYSTEM

RELATED APPLICATIONS

This application is a continuation of U.S. patent application Ser. No. 17/165,751 filed on Feb. 2, 2021 entitled Hard-Surface Disinfection System, which is a continuation of U.S. patent application Ser. No. 16/911,123 filed Jun. 24, 2020 entitled Hard-Surface Disinfection System, which is a continuation of U.S. patent application Ser. No. 16/779,351 filed Jan. 31, 2020 entitled Hard-Surface Disinfection System (now U.S. Pat. No. 10,729,979 issued Aug. 4, 2020), which is a continuation of U.S. patent application Ser. No. 16/125,642 filed Sep. 7, 2018 entitled Hard-Surface Disinfection System (now U.S. Pat. No. 10,568,981 issued Feb. 25, 2020), which is a continuation of U.S. patent application Ser. No. 15/699,219 filed Sep. 8, 2017 entitled Hard-Surface Disinfection System (now U.S. Pat. No. 10,092,665 issued Oct. 9, 2018), which is a continuation of U.S. patent application Ser. No. 15/425,585 filed Feb. 6, 2017 entitled Hard-Surface Disinfection System (now U.S. Pat. No. 9,782,505 issued Oct. 10, 2017), which is a continuation of U.S. patent application Ser. No. 15/018,440 filed Feb. 8, 2016 entitled Hard-Surface Disinfection System (now U.S. Pat. No. 9,592,312 issued Mar. 14, 2017), which is a continuation of U.S. patent application Ser. No. 14/540,869 filed Nov. 13, 2014 entitled Hard-Surface Disinfection System (now U.S. Pat. No. 9,272,059 issued Mar. 1, 2016), which is a continuation of U.S. patent application Ser. No. 14/043,465 filed Oct. 1, 2013 entitled Hard-Surface Disinfection System, (now U.S. Pat. No. 8,895,939 issued Nov. 25, 2014), which is a continuation of U.S. patent application Ser. No. 12/963,590 filed Dec. 8, 2010 entitled Hard-Surface Disinfection System (now U.S. Pat. No. 8,575,567 issued Nov. 5, 2013), which is the non-provisional of and claims priority to U.S. Provisional Application Ser. No. 61/324,257 filed Apr. 14, 2010, entitled Hard-Surface Disinfection System and to U.S. Provisional Application Ser. No. 61/267,805 filed Dec. 8, 2009, entitled Hard-Surface Disinfection System, the contents of all of which are incorporated herein in their entireties.

FIELD OF THE INVENTION

The present invention relates to systems for disinfection of hard-surfaces and related methods thereof and, more particularly, to ultraviolet light disinfection of hard-surfaces.

BACKGROUND OF THE INVENTION

Disinfection of the hard surface environment is a key factor in the constant battle to reduce infections. The emergence of multi-drug resistant organisms (MDROs) throughout the as-built environment poses a significant threat to the health and well-being of people throughout the world. MDROs in the environment contribute to rising health care costs, excessive antibiotic use and premature mortality.

Disinfecting hard surfaces, such as those found in patient areas, can be performed by exposing the hard surfaces to UVC light that is harmful to micro-organisms such as bacteria, viruses and fungi. Ultraviolet germicidal irradiation (UVGI) is an evidence-based sterilization method that uses ultraviolet (UV) light at sufficiently short wavelengths to break-down and eradicate these organisms. It is believed that the short wavelength radiation destroys organisms at a micro-organic level. It is also believed that UV light works by destroying the nucleic acids in these organisms, thereby causing a disruption in the organisms' DNA. Once the DNA (or RNA) chain is disrupted, the organisms are unable to cause infection. The primary mechanism of inactivation by UV is the creation of pyrimidine dimers which are bonds formed between adjacent pairs of thymine or cytosine pyrimidines on the same DNA or RNA strand.

There are several advantages to utilizing UV light, in addition to the effectiveness described above. UV light requires only electricity, there are no potentially hazardous chemicals and the associated storage challenges presented thereby. UV light leaves no residue, does not require drying time, cannot be spilled, requires little manpower to apply, requires very little skill on the part of the operator, and uses long-lasting bulbs that require very little inventory management.

Safely using UV light to disinfect hard surfaces does present some unique problems. First, UV light sources cast shadows. Areas in shadows may not get disinfected. Second, UV light bulbs, like nearly all light bulbs, are relatively fragile and present dangers if broken. Third, UV radiation is harmful to humans, especially in high-intensity applications like those used in disinfecting procedures.

As such, there is a need for a UV hard-surface disinfection system that exploits the advantages of UV light, while also addressing the aforementioned problems.

SUMMARY OF THE INVENTION

One aspect of the present invention provides a UV hard-surface disinfection system that is able to disinfect the hard surfaces in a room, while minimizing missed areas due to shadows. In one embodiment, a system is provided that includes multiple UV light towers. These towers can be placed in several areas of a room such that nearly all shadowed areas are eliminated.

Another aspect of the present invention provides a UV light tower design that incorporates a robustly protected light bulb, thus reducing the occurrence of broken bulbs. In one embodiment, the tower comprises a vertically oriented light bulb surrounded by a plurality, preferably three, protective blades running the length thereof. The blades preferably radiate from the bulb and are spaced 120 degrees apart. This design provides significant protection to the bulb, while minimizing interference with the light being emitted from the bulb.

In another preferred embodiment, the light bulb is surrounded and protected by a clear, quartz sleeve. In addition to protecting the bulb from accidental breakage, the sleeve induces a convection effect, like a chimney. As the bulb heats, cool air is drawn through vents in the bottom of the sleeve, heated and exhausted through the top of the sleeve. This circulation cools the bulbs, extending their life and protecting users from accidental burns.

In order to further protect the bulb, another aspect of the present invention provides a tower that has a relatively wide base and a very low center of gravity. This design is a safety feature that creates stability and reduces the possibility of a tower tipping over while it is being moved.

In yet another aspect of the present invention there is provided a UV disinfection system that minimizes UV light exposure to humans during operation. In a preferred embodiment, the system is able to be controlled remotely, such that during activation of the system, no operator is present in the room.

In another preferred embodiment, one or all towers are outfitted with safety devices that cut power to all towers in the event that a person enters the room. More preferably, the safety device includes motion-detecting capability, such that the safety shutdown response is automatic. In a preferred embodiment, the motion detection capability incorporates a laser scanner, providing an extremely accurate motion detection capability that is more thorough and less prone to false positives than other motion detection scanners such as infra-red devices.

Another aspect of the present invention provides a control cart that is constructed and arranged to transport a plurality of towers. The cart is low to the ground such that the towers may be loaded and unloaded easily by a single operator. Alternatively, the towers may be linked together with the cart to form a chain. This embodiment allows the towers to support themselves continuously, while being transported by pushing or pulling the cart. This embodiment also allows the use of a hand-cart attachment, which provides a solution to moving all of the units from one room to another without requiring that they be reloaded onto the control cart, which may be left in a single location, such as a hallway, in proximity to both rooms.

One embodiment provides a cart that includes a control panel that can be used to remotely control various parameters of each of the towers, as well as provide various diagnostic data to the user.

DETAILED DESCRIPTION OF THE INVENTION

Figure 1:
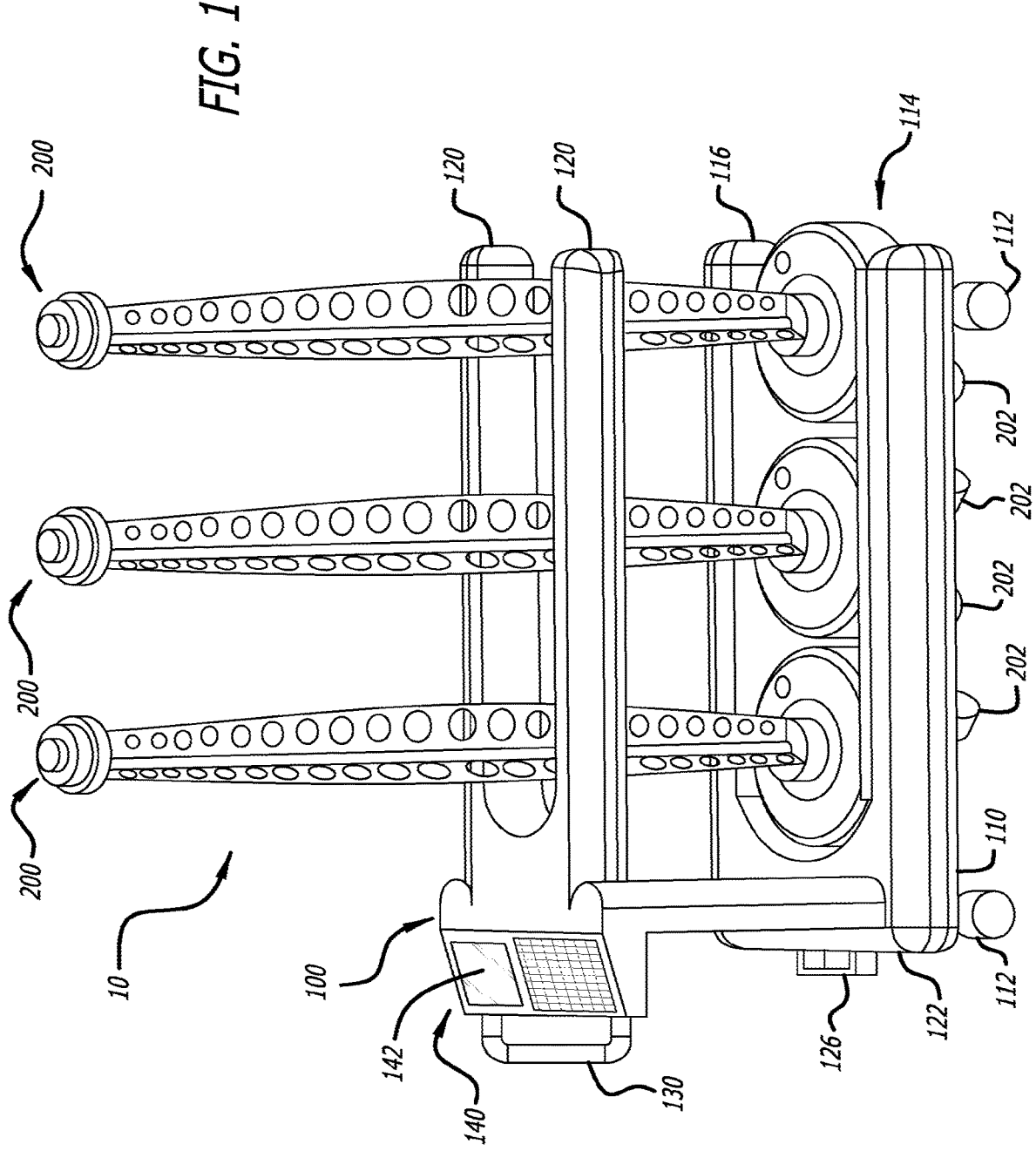
FIG. 1 is a perspective view of an embodiment of a system of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to the figures and first to FIG. 1, there is shown an embodiment of a system 10 of the present invention. System 10 generally includes a control station or cart 100 and a plurality of light assemblies or towers 200, shown as loaded onto the cart 100.

The cart 100 generally includes a carriage 110 supported by a plurality of casters 112, and defining a cutout 114 shaped to receive and secure the towers 200 for transport. The distal end 116 of the cutout 114 is open such that the towers may be easily loaded onto and off of the cart 100. The cutout 114 may include a complete floor (not shown) onto which wheels 202 of the towers 200 (see FIG. 2) may be rolled.

More preferably, however, the cutout 114 has an open bottom and a supporting ridge that slightly elevates the wheels 202 off the ground. This design provides a secure relationship between the cart 100 and the towers 200. Many hospitals include ramped areas. Disabling the wheels 202 by elevating the towers 200 prevents the towers from rolling off of the cart 100.

Figure 2:
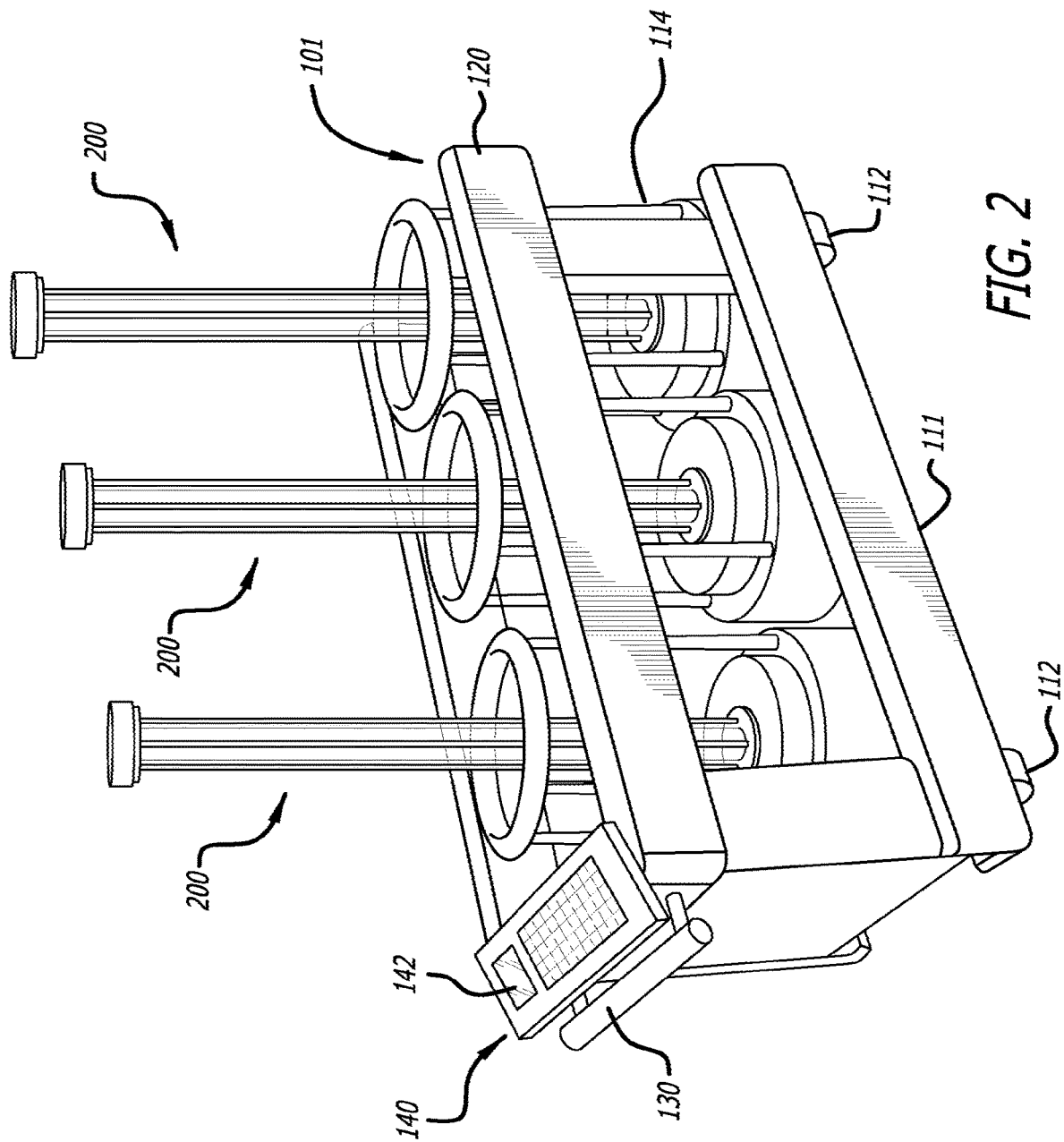
FIG. 2 is a perspective view of an embodiment of a system of the present invention.

Alternatively, as shown in FIG. 2, an embodiment 101 of the cart has a carriage 111 that allows the the towers 200 to remain in contact with the ground, rather than being elevated. The towers in this embodiment are preferably linked together for transport, with at least one tower being linked or otherwise attached to the cart 100.

The cart 100 or 101 may also include a pair of safety arms 120 that extend along the length of the cart 100 or 101 on other side of the towers 200 when the towers 200 are loaded onto the cart 100 or 101. Aesthetically, the arms may match the cutout 114 of the carriage 110 or 111. Functionally, the arms 120 provide protection against accidentally impacting the towers against objects or people as the towers 200 are being transported on the cart 100 or 101.

In one embodiment, at a proximal end 122 of the cart 100, there is a foot jack 126. The foot jack 126 is usable to elevate the cart 100 enough to raise the wheels 202 off the ground. In this way, the wheels 202 of the towers 200 may be used to roll the towers 200 into the cutout 114. Once the towers 200 are in place within the cutout 114, the foot jack 126 is depressed, raising the towers 200 off the ground. When it is desired to deploy the towers 200, the foot jack 126 is released and the cart 100 lowers the towers 200 such that the wheels 202 are again in contact with the ground.

Also at the proximal end 122 of the cart 100 or 101, there is a handle 130 and a control panel 140. The control panel 140 may include a display 142 usable to display a variety of parameters relevant to the safe operation of the towers 200. The parameters include, but are not limited to: ambient room temperature, room dimensions, fluence level, disinfection time, input current and voltage, and maintenance information such as bulb run time. Additionally, the control panel may be used to upload, preferably wirelessly, data to a hospital information system regarding the sanitization of a given room. It is also envisioned that the control panel would have a communications ability that is compatible with the LMS (or similar) system found in many hospitals (smart scanner system to evaluate distance and occupancy) e.g. the LMS can map the room and an algorithm could calculate emitter run times.

Figure 3:
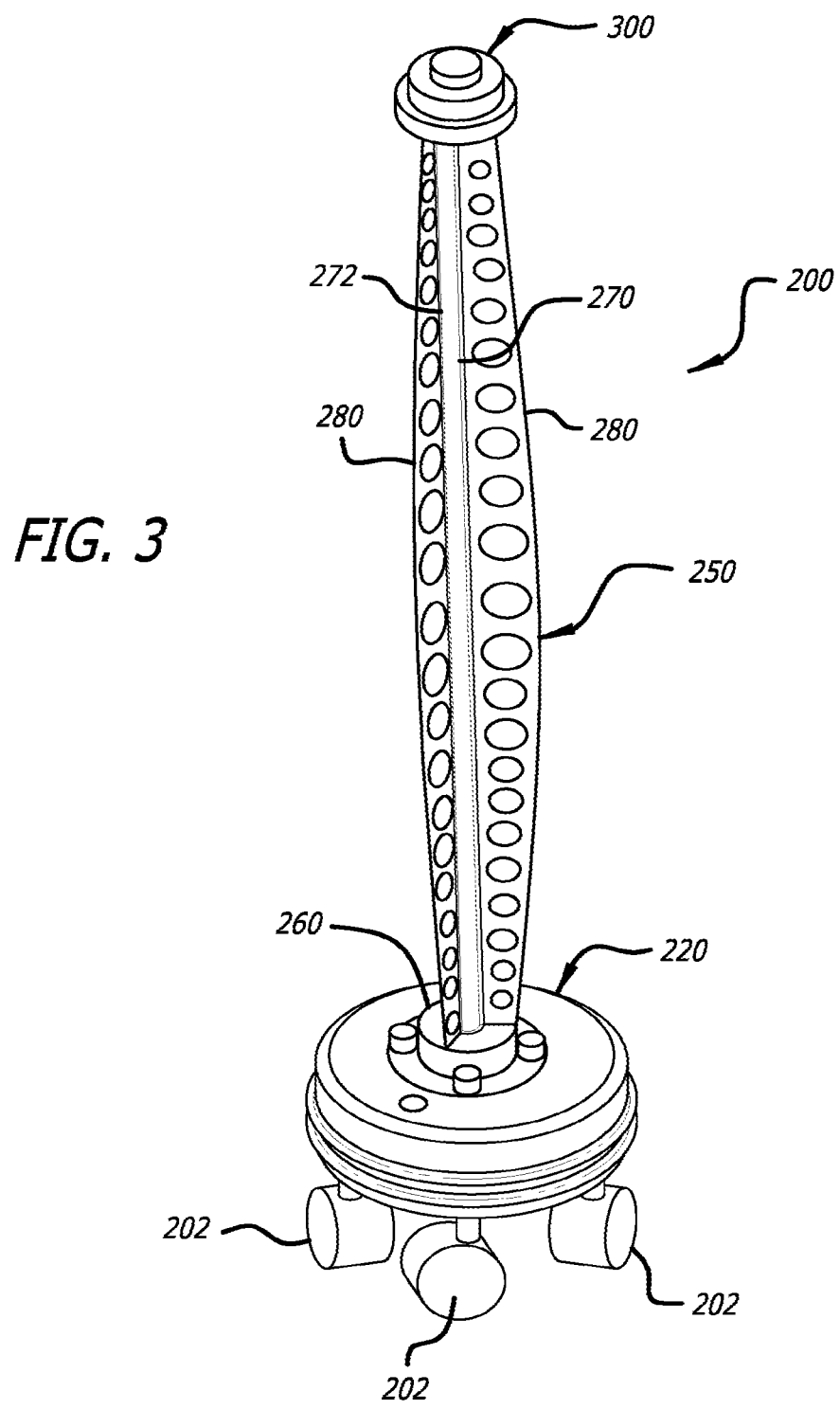
FIG. 3 is a perspective view of an embodiment of a light tower of the present invention.

One embodiment of a light tower 200 is shown in FIG. 3. The light tower 200 generally includes a base 220 supported by a plurality of wheels 202, a tower assembly 250, and a cap 300.

Figure 4:
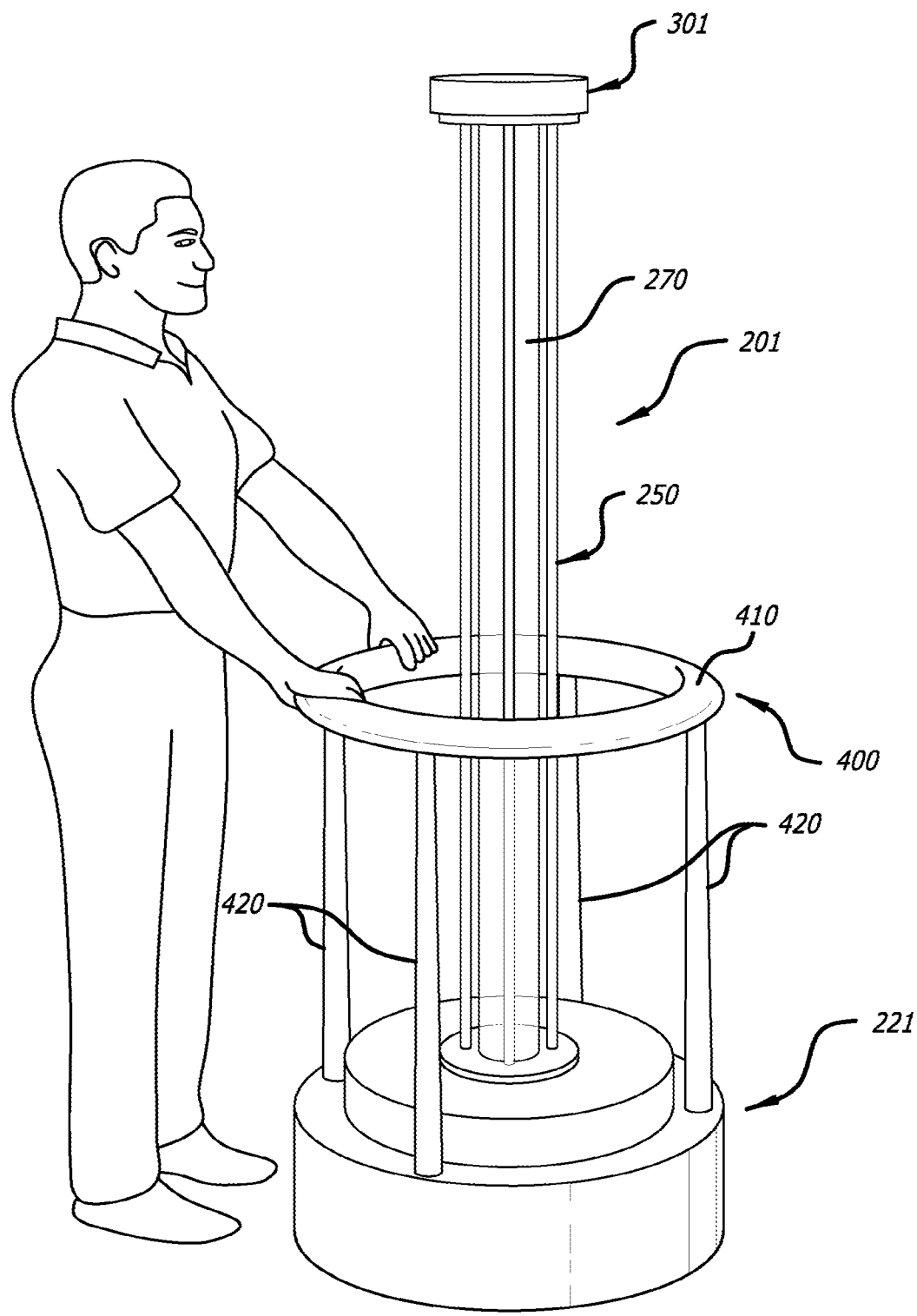
FIG. 4 is a perspective view of an embodiment of a light tower of the present invention in a first configuration.
Figure 5:
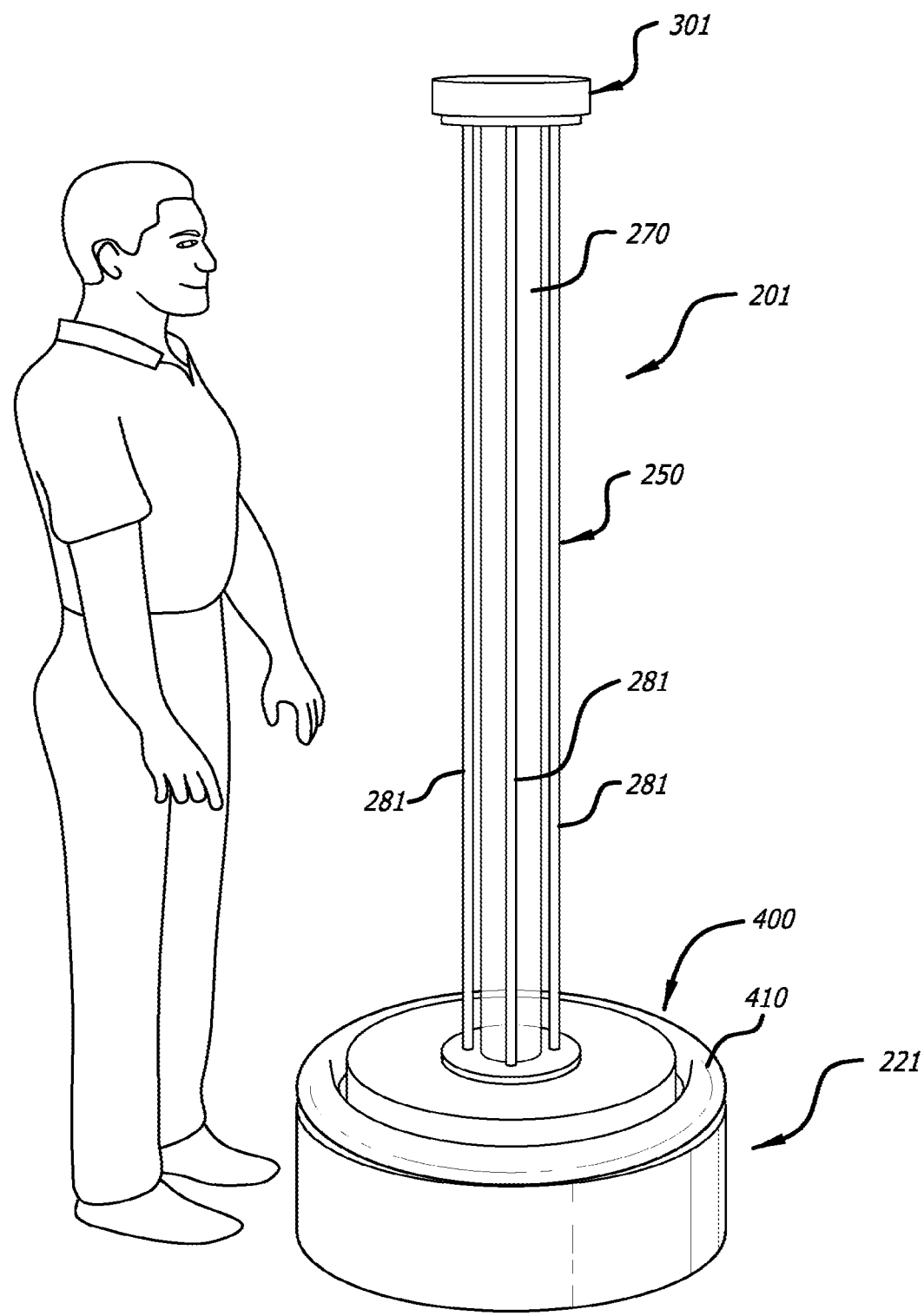
FIG. 5 is a perspective view of the light tower of FIG. 5 in a second configuration.
Figure 6:
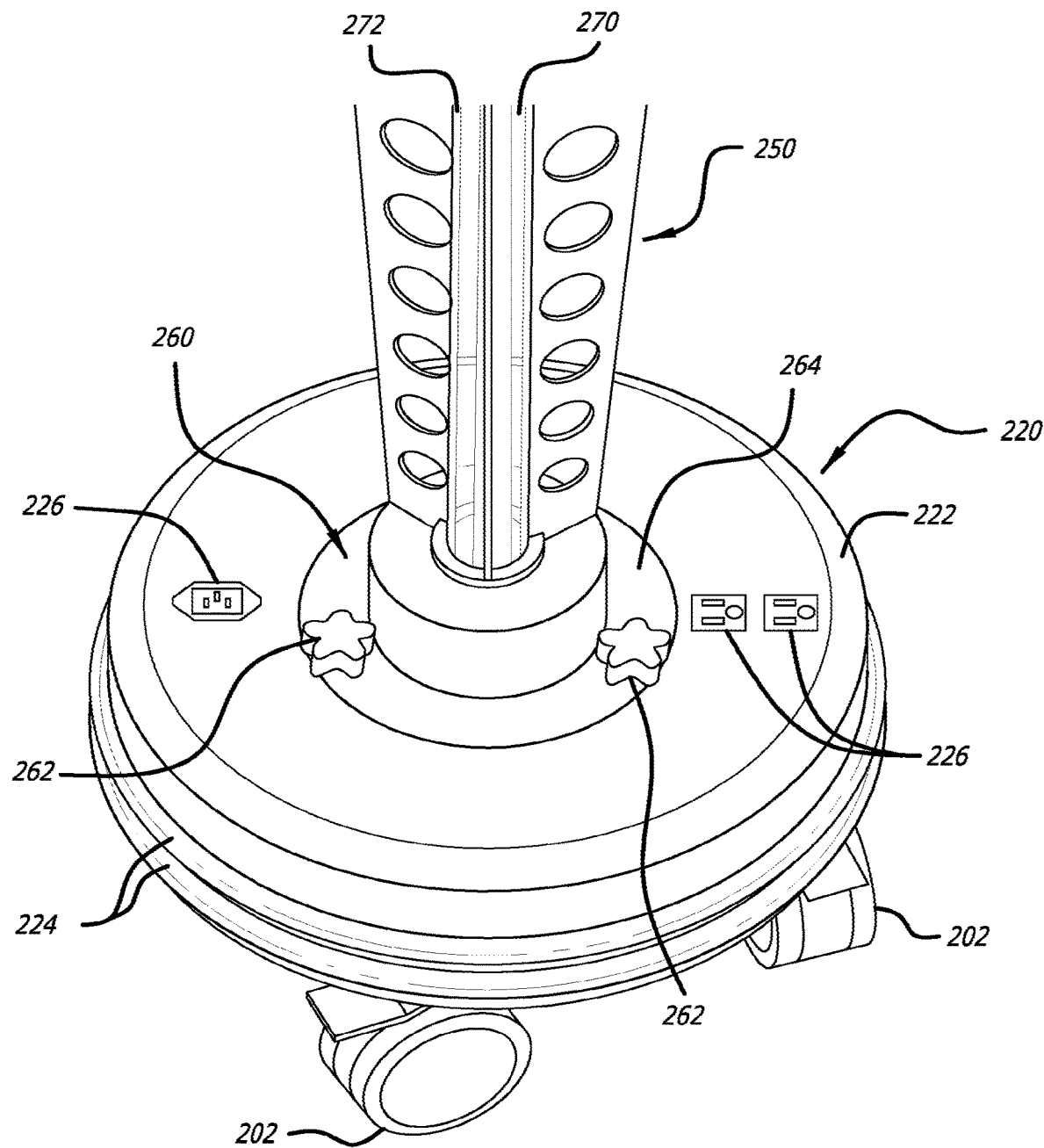
FIG. 6 is a perspective view of an embodiment of a base of a light tower of the present invention.

Another embodiment of a light tower 201 is shown in FIG. 4. The light tower 201 includes a base 221 and is supported by a plurality of wheels 202, a tower assembly 251, and a cap 301, but also has a push ring 400 assembly for use in moving the light tower 201 without applying pressure to the light source 270. The push ring 400 preferably includes a handle 410 and a plurality of telescoping supports 420. The telescoping supports 420 allow the push ring to be stowed in an active configuration, shown in FIG. 5, when the light source 270 is activated. Because the push ring 400 is lowered in the active position, it does not interfere with the light beams emitted by the light source 270, thereby ensuring no shadows are created by the push ring assembly.

Electronics may be utilized to prevent the activation of the light source, and/or emit a warning, if the push ring is in the up position. Alternatively, the telescoping arms 420 may be automatically activated such that they lower themselves prior to activating the light source and raise themselves upon completion.

Reference is now made to FIGS. 6-9, which show details of embodiments 220 and 221 of the base, respectively. Notably, shared features between the two are indicated by common reference numerals. It is also understood that in these Figures, and throughout the specification, that features may be interchangeable between embodiments. The base 220 or 221 is comprised of a housing 222 or 223 that contains power circuitry for the tower 200 or 201. Preferably, the housing 222 or 223 is round so that the tower 200 or 201 may be easily docked within the cart 100 or 101 without regard to angular orientation. The housing 222 or 223 may optionally include one or more bumpers 224 (shown associated with housing 222) to protect the base 220 or 221 as well as anything the base 220 or 221 may contact.

The base 220 or 221 may also include one or more power connections 226. Providing a plurality of power connections 226 allows one of the towers 200 or 201 (designated herein as the "master" tower) to be connected into a standard outlet. The remaining towers may then be "daisy-chained" to the master such that power to all of the towers 200 or 201 may be controlled by the cart 100 or 101. This results in a redundant safety relay in the base 220 or 221 of the master to control power to all down-stream units that are connected together. The power connections 226 are shown in the Figures as being female outlets but one skilled in the art will realize that this is merely a convention of convenience and not to be interpreted as limiting.

The tower assembly 250 generally includes a base connector assembly 260, a light source 270, and, optionally, a plurality of protective blades 280. The base connector assembly 260 connects the bottom of the tower assembly 250 to the base 220 or 221. The base connector assembly 260 includes one or more connectors 262, shown in FIG. 6 in non-limiting example as hand screws, and in FIG. 7 in non-limiting example as bolts or machine screws, and a light socket 264. Preferably, the connectors 262 may be secured and released without the use of tools for ease of bulb replacement and other maintenance. Most importantly, the light socket 264 securely connects the tower assembly 250 to the base 220 and is sturdy enough to withstand lateral forces placed on the tower assembly 250.

The light source 270 may be any appropriately shaped UV light source, capable of emitting sufficient light for purposes of sanitizing a room. Non-limiting examples include a low pressure amalgam light source, preferably with a solarization-reducing coating. Foreseeably, an LED UV light source would draw less power and may be optimally suited to battery-powered towers 200. The light source 270 preferably includes a variable output transformer 271 (see FIG. 7). The variable output transformer 271 controls the output power of the light source 270.

Figure 7:
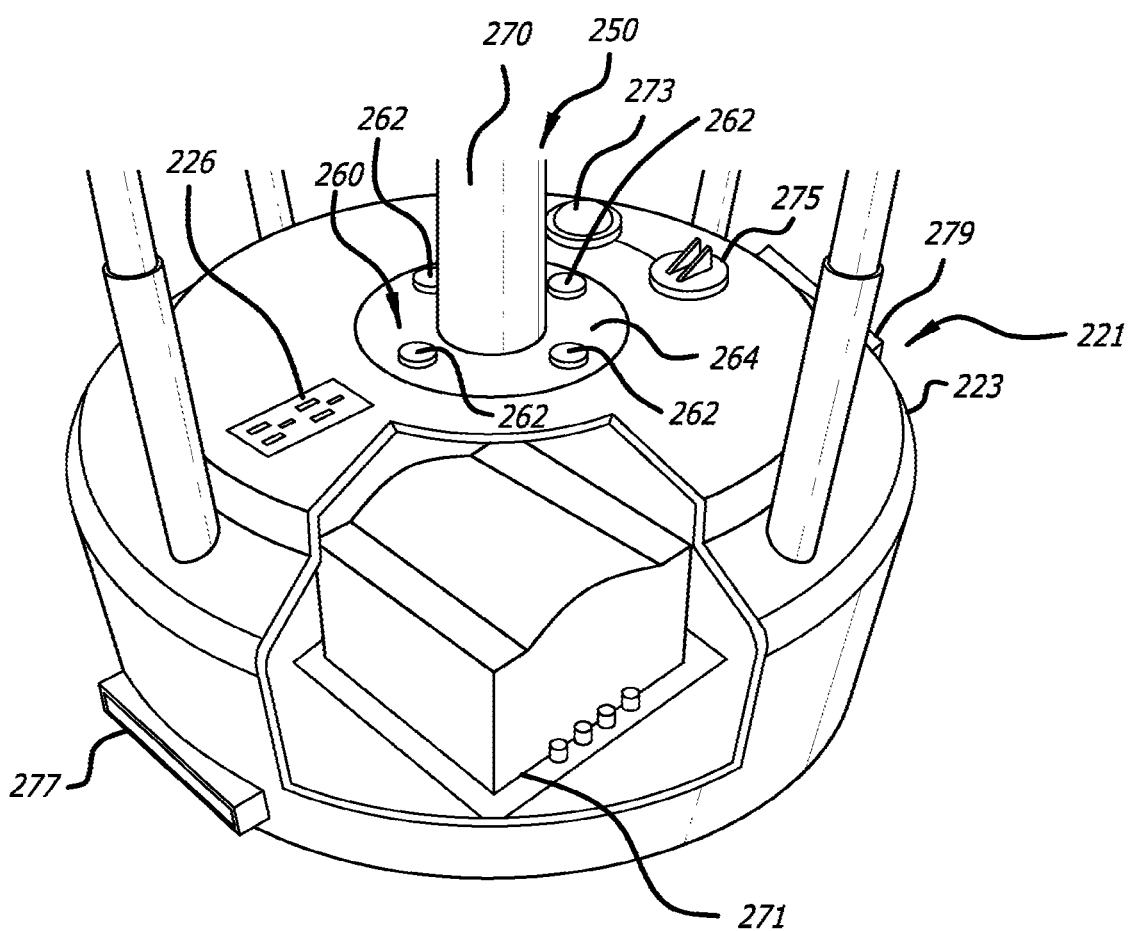
FIG. 7 is a perspective view of an embodiment of a base of a light tower of the present invention.

As shown in FIG. 7, the base 220 or 221 may also include a fluency sensor 273. This sensor 273 monitors the power output of the light source 270 to ensure that it maintains an output over a threshold, which may be either an absolute threshold, or a range within a set power output. If the light source 270 has a power output that drops below this threshold, the sensor 273 sends a signal to the control panel 140 indicating a lower power output status of a given tower 200 or 201. This may indicate a bad bulb or other problem that may result in compromised disinfection if the condition is not repaired.

Also shown in FIG. 7 is a lockout disconnect 275. This is a mechanical power switch that accommodates a padlock that, when in place, prevents the power switch from being turned to an on position. This ensures a tower 200 or 201 may not be inadvertently activated.

Figure 8:
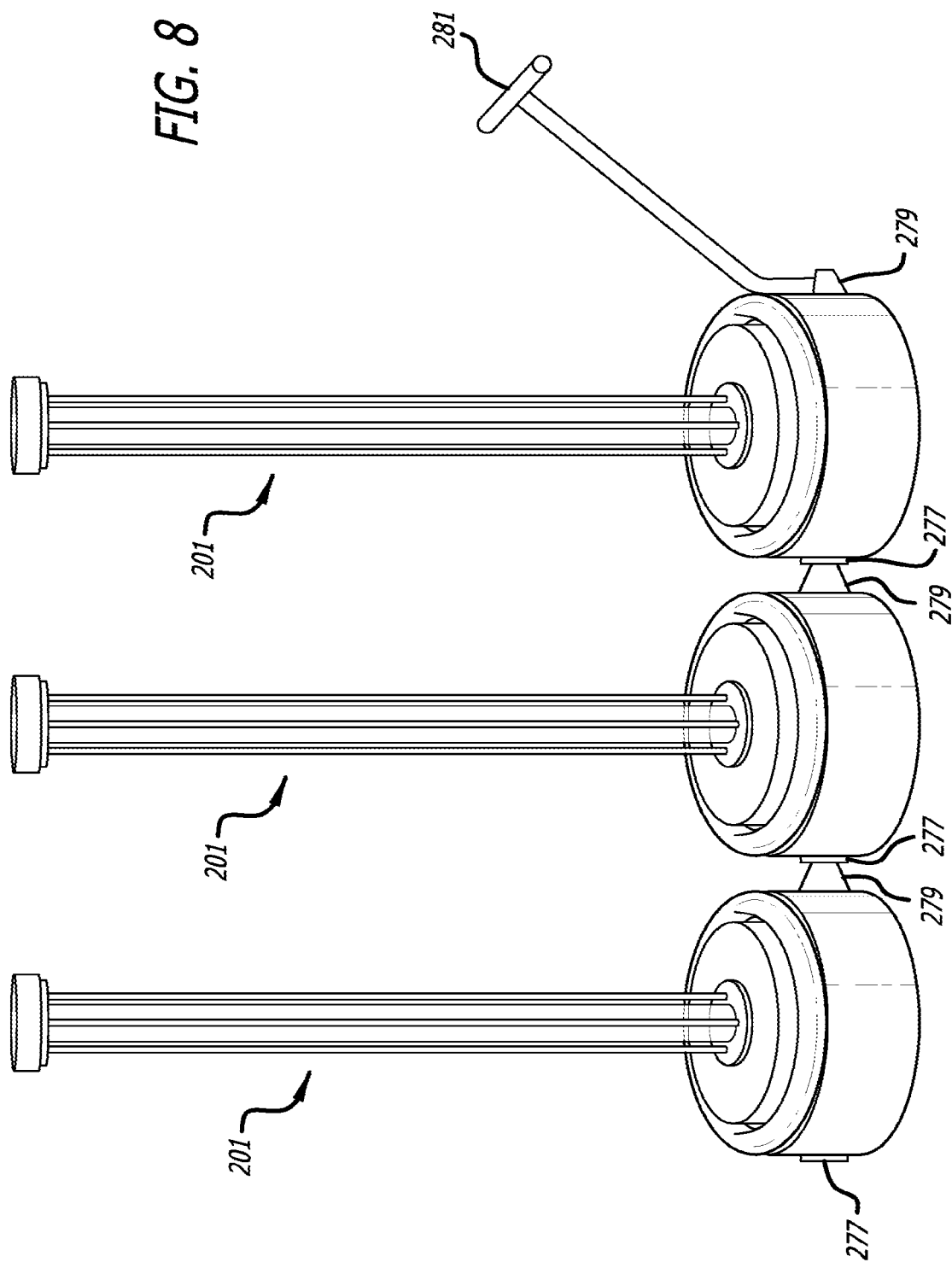
FIG. 8 is a perspective view of an embodiment of a light tower of the present invention connected to two other light towers and a hand cart of the present invention.

Shown also in FIG. 7 is a mechanical linkage 277 that allows the base 221 to be mated with another base 221. The linkage 277 is a female linkage. A corresponding male linkage 279 is on the other side of the base 201. As discussed above, these linkages 277 and 279 provide a convenient means for transporting the towers 200 or 201 from room to room. FIG. 8 shows three towers 201 connected together with linkages 277 and 279 and a handle 281 configured to mate with a male connector 279 or a female connector 277.

Figure 9:
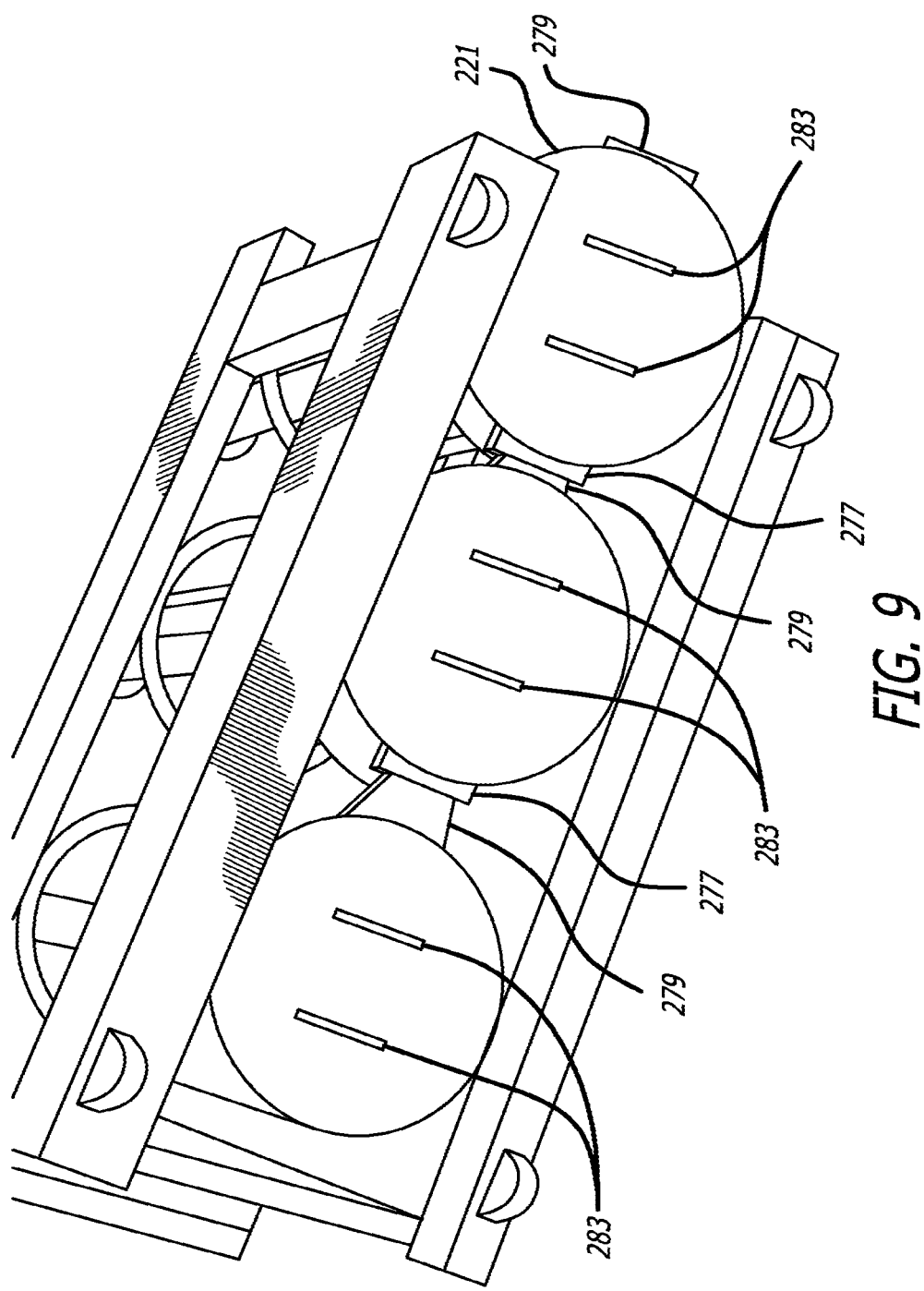
FIG. 9 is a bottom perspective view of an embodiment of a light tower of the present invention loaded into a controller cart with two other light towers.

FIG. 9 shows an embodiment of a bottom of base 220 or 221 that includes one or more floor lamps 283. The floor lamps 283 provide disinfecting light under the bases 220 or 221 to ensure there are no shadows created by the units themselves, and also that contaminants are not dragged from room to room by the towers 200 or 201.

Though the light source 270 is shown as being vertically-oriented, it is envisioned that the light source 270 may be angled or even oscillating to further reduce shadows.

The selection of a lamp is a significant factor in determining the footprint of the system 10. The physical layout of a patient care area will provide obstacles to the UVC emissions. These obstacles will produce shadows on surfaces and therefore reduce the effectiveness of the system in certain areas of the patient care area. The system 10 footprint is flexible so that it can be deployed in such a way to overcome these shadows. Satellite rooms such as the washroom attached to a patient care area will also pose a challenge to the system as these areas have a high probability of containing micro-organisms that could lead to a Hospital Acquired Infection. The UVC reflective properties of materials are not the same as that of visible light. The systems will be deployed in existing patient care areas so selection of materials with a high degree of UVC reflectivity is not an option. The system's repeatability will suffer if system depends on reflected UVC light to overcome shadows from obstacles in the room.

The light source 270 is preferably surrounded by a protective sleeve 272. The protective sleeve may be constructed of any suitable clear material capable and very efficient at passing UVC as well as protecting the bulb against impact without significantly interfering with the light being emitted.

In a preferred embodiment the protective sleeve 272 comprises a quartz sleeve, synthetic quartz sleeve or similar synthetic material to provide stability to the bulb as to not restrict light and/or create shadow. It has been noted that using a quartz sleeve 272 creates a protective temperature barrier to reduce the severity and/or occurance of skin burns.

Because the sleeve 272 is significantly cooler than the bulb surface, using a sleeve 272 may also reduce odors due to dust and other particulates landing on the bulb and burning.

It is known that the sleeve 272 creates a chimney effect in that heat coming off the light source 270 rises forcing cool convection air to be drawn upward through the sleeve 272 from the bottom. It may be beneficial to provide a forced cooling system, in which a fan could be provided in-line with the top or bottom of the sleeve 272.

In most applications, the quartz sleeves 272 provide sufficient protection against accidental breakage. However, some applications may warrant a more robust design. As such, one embodiment of the present invention provides a light source 270 that further includes a plurality, preferably three, protective blades 280 radiating from the light source 270 (e.g. FIG. 3) or guidewires 281 (e.g. FIG. 5). The blades or guidewires 280 or 281 may be any acceptably light, yet strong material, such as aluminum, plexiglass, or the like. A clear material may reduce shadows but, due to the thin construction and radiating orientation of the blades 280, they have very little effect on the light emission capabilities of the light source 270. Shown are three blades 280, spaced 120 degrees apart, and including a plurality of circular cutouts used to increase stiffness and reduce weight, or four guidewires 281 space 90 degrees apart.

Figure 10:
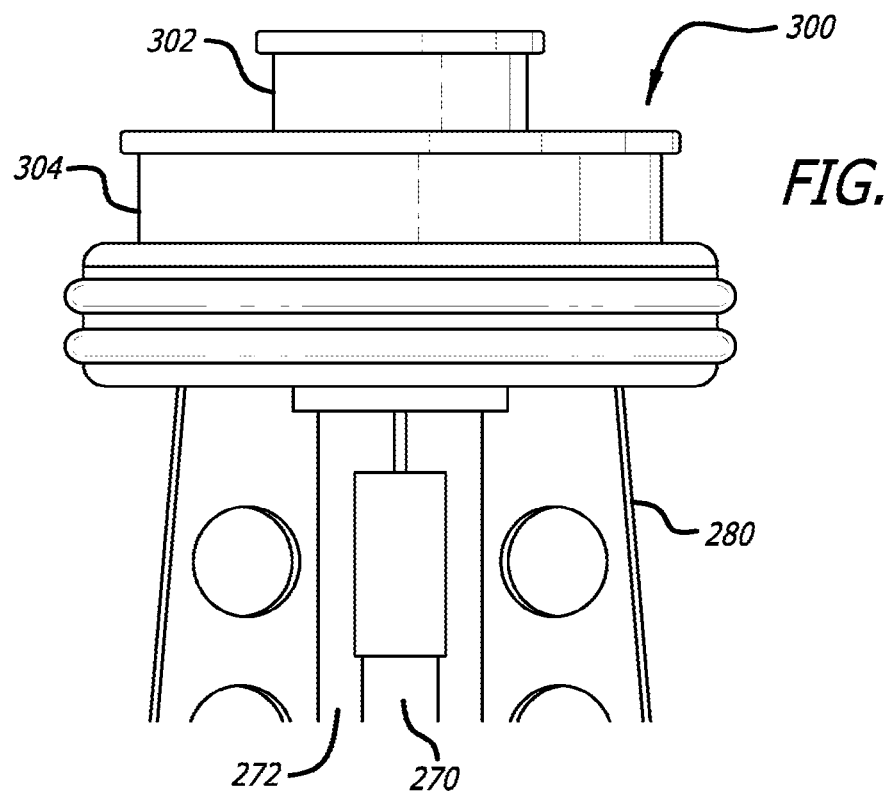
FIG. 10 is a partial elevation view showing an embodiment of a tower cap of a light tower of the present invention.
Figure 11:
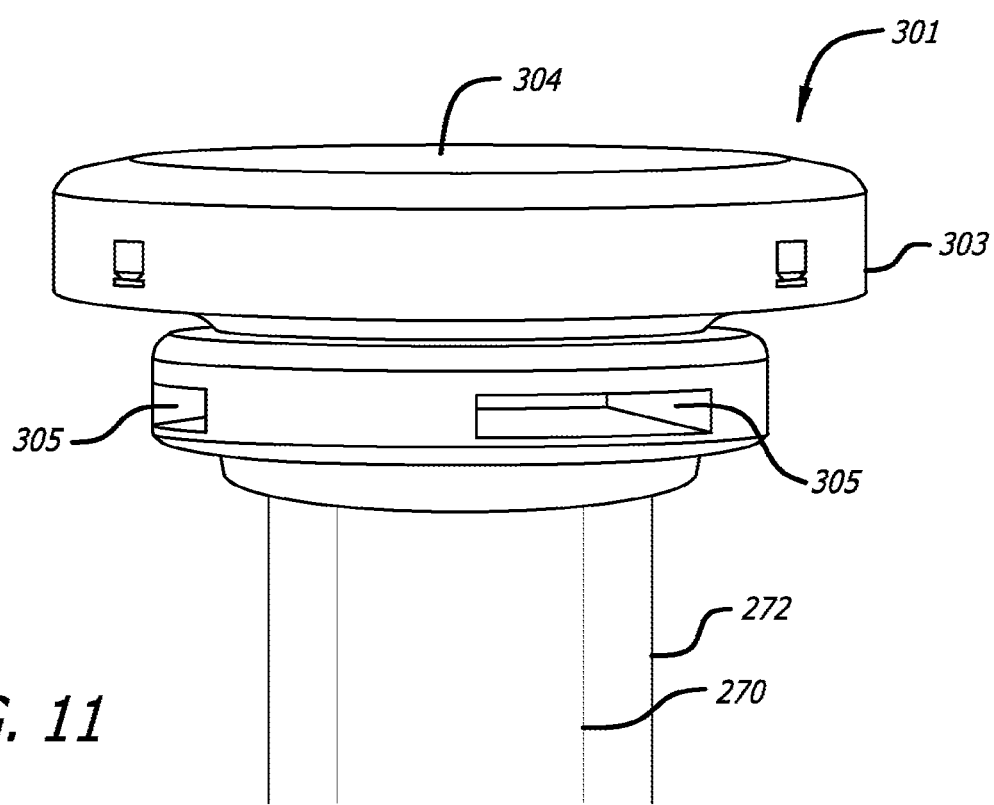
FIG. 11 is a partial elevation view showing an embodiment of a tower cap of a light tower of the present invention.

Referring now to FIGS. 10 and 11, there are shown two embodiments 300 and 301 of the cap assembly at the top of the tower assembly 250. The cap assembly 300 or 301 is used to secure the various components of the tower assembly 250 together. The cap assembly 300 or 301 also preferably houses a safety sensor 302 or 303, preferably a motion detector that senses if a person has entered a room and disables the tower. This motion detector could be an infrared motion detector, such as those found in many security systems, or it could be a dual motion detector, a door curtain or the like. Preferably, the safety sensor 302 or 303 includes a motion detector that uses lasers that scan the surrounding area. A preferred embodiment of the cap assembly 301, shown in FIG. 11, utilizes a safety sensor 303 that overhangs the rest of the cap assembly 301 such that the sensor can "see" virtually straight down, giving the sensor nearly 180 degrees of vertical coverage, as well as 360 degrees of coverage in a horizontal plane. As such, safety sensor 303 has nearly complete spherical coverage with exception of the area directly under the base, which would not encounter motion.

In a preferred embodiment, the cap assembly 300 or 301, or the base assembly 220 or 221,also includes a communications module 304. The communications module 304 communicates via any acceptable medium such as radio, wifi, microwaves, Bluetooth®, etc., with the cart 100 or 101, and optionally the other towers 200 or 201. Thus, if one sensor 302 or 303 senses movement, a signal could be sent to the other towers 200 or 201 to shut down. Alternatively, a signal could be sent to the cart 100 or 101, which would in turn shut the remaining towers 200 or 201 down.

The sensor 302 or 303 may also be used to detect and monitor the fluence level of the UV emissions (unless the base includes a fluence sensor such as the fluence sensor 273 on base 221) to confirm that the tower 200 or 201 is operating at a desired level. These sensors can be used in conjunction with an amplifier to transmit the data to a control device that will integrate the irradiance level to obtain the fluence level received at the sensor. Single point photosensors are sensitive to the angle of light incidence.

Preferably, the tower 200 or 201 also includes a speaker (not shown) in either the communications module 304 or the base 220 or 221 that creates an audible warning before the light source 270 is energized. It is also envisioned that the communications module 304, may be used to electronically measure the room to determine the appropriate output necessary by the tower 200 to adequately sanitize the space. This feature ensures that energy is not wasted and bulb life and safety are maximized.

The cap assembly 301 shown in FIG. 11 also includes one or more vents 305 in fluid communication with an interior of the protective sleeve 272 to allow air heated by the lamp 270 to escape.

Although the invention has been described in terms of particular embodiments and applications, one of ordinary skill in the art, in light of this teaching, can generate additional embodiments and modifications without departing from the spirit of or exceeding the scope of the claimed invention. For example, the system of the present invention might be well-suited for applications outside of healthcare. Non-limiting examples include locker rooms and other athletic facilities, daycares, prisons etc. Accordingly, it is to be understood that the drawings and descriptions herein are proffered by way of example to facilitate comprehension of the invention and should not be construed to limit the scope thereof.

The invention claimed is:

1. A method of disinfecting a room comprising:
    rolling a plurality of ultraviolet-emitting assemblies into a room by rolling a cart containing the plurality of ultraviolet-emitting assemblies into the room;
    positioning each of the plurality of ultraviolet-emitting assemblies in separate locations selected to minimize shadows created by objects in the room;
    establishing wireless data communications between the plurality of ultraviolet-emitting assemblies and a remote control;
    activating the plurality of ultraviolet-emitting assemblies using the remote control, thereby disinfecting the room with ultraviolet energy emitted from the plurality of assemblies.

2. The method of claim 1 wherein positioning each of the plurality of ultraviolet-emitting assemblies in separate locations selected to minimize shadows created by objects in the room comprises placing each of the plurality of ultraviolet-emitting assemblies on different sides of objects in the room.

3. The method of claim 1 further comprising ensuring safe operation of the plurality of ultraviolet-emitting assemblies by sounding an audible alarm prior to emitting energy from the plurality of ultraviolet-emitting assemblies.

4. A method of disinfecting a room comprising:
    rolling a plurality of ultraviolet-emitting assemblies into a room by utilizing casters on which each of the plurality of ultraviolet-emitting assemblies is supported to roll each of the plurality of ultraviolet-emitting assemblies into the room independently;
    positioning each of the plurality of ultraviolet-emitting assemblies in separate locations selected to minimize shadows created by objects in the room;
    establishing wireless data communications between the plurality of ultraviolet-emitting assemblies and a remote control;
    activating the plurality of ultraviolet-emitting assemblies using the remote control, thereby disinfecting the room with ultraviolet energy emitted from the plurality of assemblies.

5. The method of claim 4 wherein positioning each of the plurality of ultraviolet-emitting assemblies in separate locations selected to minimize shadows created by objects in the room comprises placing each of the plurality of ultraviolet-emitting assemblies on different sides of objects in the room.

6. The method of claim 4 further comprising ensuring safe operation of the plurality of ultraviolet-emitting assemblies by sounding an audible alarm prior to emitting energy from the plurality of ultraviolet-emitting assemblies.

7. The method of claim 4 further comprising ensuring safe operation of the plurality of ultraviolet-emitting assemblies by shutting off the plurality of ultraviolet energy emitters if motion is detected in the room.

8. A method of disinfecting a room comprising:
rolling a plurality of ultraviolet-emitting assemblies into a room;
positioning each of the plurality of ultraviolet-emitting assemblies in separate locations selected to minimize shadows created by objects in the room by placing each of the plurality of ultraviolet-emitting assemblies on different sides of objects in the room;
establishing wireless data communications between the plurality of ultraviolet-emitting assemblies and a remote control;
activating the plurality of ultraviolet-emitting assemblies using the remote control, thereby disinfecting the room with ultraviolet energy emitted from the plurality of assemblies.

9. The method of claim 8 wherein rolling a plurality of ultraviolet-emitting assemblies into a room comprises rolling a cart containing the plurality of ultraviolet-emitting assemblies into the room.

10. The method of claim 8 further comprising ensuring safe operation of the plurality of ultraviolet-emitting assemblies by sounding an audible alarm prior to emitting energy from the plurality of ultraviolet-emitting assemblies.

* * * * *